US012674138B2

(12) United States Patent (10) Patent No.: US 12,674,138 B2
Lee et al. (45) Date of Patent: *Jul. 7, 2026

(54) METHOD FOR THE INDUCTION AND EXPANSION OF NATURAL KILLER CELLS DERIVED FROM PERIPHERAL BLOOD MONONUCLEAR CELLS

(71) Applicant: NKMAX Co., Ltd., Seongnam-Si (KR)

(72) Inventors: Kyung Mi Lee, Seoul (KR); Seon Ah Lim, Seoul (KR); Cassian Yee, Seoul (KR)

(73) Assignee: NKMAX Co., Ltd., Seongnam-Si (KR)

( * ) Notice: Subject to any disclaimer, the term of this patent is extended or adjusted under 35 U.S.C. 154(b) by 433 days.

This patent is subject to a terminal disclaimer.

(21) Appl. No.: 15/948,619

(22) Filed: Apr. 9, 2018

(65) Prior Publication Data

US 2018/0223257 A1 Aug. 9, 2018

Related U.S. Application Data

(62) Division of application No. 14/399,371, filed as application No. PCT/KR2013/003981 on May 7, 2013, now Pat. No. 9,938,498.

(30) Foreign Application Priority Data

May 7, 2012 (KR) ........................ 10-2012-0048165
May 7, 2013 (KR) ........................ 10-2013-0051442

(51) Int. Cl.
*C12N 5/0783* (2010.01)
*A61K 35/17* (2025.01)
*A61K 40/15* (2025.01)
*A61K 40/46* (2025.01)

(52) U.S. Cl.
CPC ............ *C12N 5/0646* (2013.01); *A61K 40/15* (2025.01); *A61K 40/46* (2025.01); *C12N 2501/2302* (2013.01); *C12N 2502/1114* (2013.01); *C12N 2502/30* (2013.01)

(58) Field of Classification Search
CPC .............................. C12N 5/0646; A61K 35/17
See application file for complete search history.

(56) References Cited

U.S. PATENT DOCUMENTS

| | | | |
|---|---|---|---|
| 4,645,830 A | 2/1987 | Yasushi et al. | |
| 5,415,874 A | 5/1995 | Bender et al. | |
| 6,194,204 B1 | 2/2001 | Crawford et al. | |
| 6,261,839 B1 | 7/2001 | Multhoff et al. | |
| 7,544,355 B2 | 6/2009 | Velardi | |
| 7,829,075 B2 | 11/2010 | Novak et al. | |
| 8,257,970 B2 | 9/2012 | Lowdell | |
| 8,318,491 B2 | 11/2012 | Choi et al. | |
| 8,637,308 B2 | 1/2014 | Lowdell | |
| 8,877,182 B2 | 11/2014 | Alici | |
| 8,926,964 B2 | 1/2015 | Hariri et al. | |
| 9,121,008 B2 | 9/2015 | Tsai | |
| 9,175,266 B2 | 11/2015 | Peled et al. | |
| 9,222,072 B2 | 12/2015 | Chang | |
| 9,260,696 B2 | 2/2016 | Kaufman et al. | |
| 9,404,083 B2 | 8/2016 | Yonemitsu et al. | |
| 9,464,274 B2 | 10/2016 | Hariri et al. | |
| 9,623,082 B2 | 4/2017 | Copik et al. | |
| 9,655,925 B2 | 5/2017 | Lowdell | |
| 9,834,753 B2 | 12/2017 | Min et al. | |
| 9,938,498 B2 | 4/2018 | Lee et al. | |
| 10,151,745 B2 | 12/2018 | Hermine et al. | |
| 10,195,231 B2 | 2/2019 | Liao et al. | |
| 10,300,089 B2 | 5/2019 | Copik et al. | |
| 10,450,547 B1 | 10/2019 | Sun et al. | |
| 10,463,715 B2 | 11/2019 | Copik et al. | |
| 10,590,385 B2 * | 3/2020 | Park ........................ A61P 31/04 |
| 10,774,311 B2 | 9/2020 | Campana et al. | |
| 10,864,245 B2 | 12/2020 | Romagnani et al. | |
| 11,066,644 B2 | 7/2021 | Park et al. | |
| 11,110,126 B2 | 9/2021 | Lee et al. | |

(Continued)

FOREIGN PATENT DOCUMENTS

| | | |
|---|---|---|
| CN | 102533648 A | 7/2012 |
| CN | 104705291 | 6/2015 |

(Continued)

OTHER PUBLICATIONS

Lee et al., machine translation for KR-10-2012-0016427, published Feb. 24, 2012, pp. 1-32. (Year: 2012).*
Edited by Mary L. Disis, Immunotherapy of Cancer, Humana Press, 2006, Chapter 3/ NK Cells and Cancer Immunotherapy, pp. 47-51. (Year: 2006).*
Lim et al., "GMP-Compliant, Large-Scale Expanded Allogeneic Natural Killer Cells Have Potent Cytolytic Activity against Cancer Cells In Vitro and In Vivo", LPOS, Jan. 2013, vol. 8, No. 1, e53611, pp. 1-9. (Year: 2013).*
Marquedant, Katie, "Study reveals how to activate natural killer cells to protect against cancer and other diseases", https://www.massgeneral.org/news/press-release/study-reveals-how-to-activate-natural-killer-cells-to-protect-against-cancer#, 2022, pp. 1-6. (Year: 2022).*

(Continued)

*Primary Examiner* — Laura Schuberg
(74) *Attorney, Agent, or Firm* — KNOBBE, MARTENS OLSON & BEAR, LLP

(57) ABSTRACT

The present invention relates to a method for inducing and expanding natural killer cells derived from peripheral blood mononuclear cells, which comprises co-culturing, as feeder cells, irradiated Jurkat cells and irradiated Epstein-Barr virus transformed lymphocyte continuous line (EBV-LCL) cells in the presence of cytokines, along with peripheral blood mononuclear cells. According to the present invention, a large quantity of natural killer cells can be induced and proliferated from a small quantity of peripheral blood mononuclear cells even without the use of high-cost equipment or various kinds of expensive cytokines, thereby making it possible to significantly improve the efficiency and efficacy of the prevention and treatment of cancer using the natural killer cells.

15 Claims, 6 Drawing Sheets

(56) References Cited

U.S. PATENT DOCUMENTS

| | | | |
|---|---|---|---|
| 11,504,396 B2 | 11/2022 | Kim et al. | |
| 12,098,388 B2 | 9/2024 | Park et al. | |
| 2003/0068306 A1 | 4/2003 | Dilber | |
| 2004/0173778 A1* | 9/2004 | Roncarolo | A61P 37/02 |
| | | | 252/387 |
| 2004/0224402 A1* | 11/2004 | Bonyhadi | A61K 39/464838 |
| | | | 435/372 |
| 2005/0191743 A1 | 9/2005 | Wu et al. | |
| 2006/0067914 A1 | 3/2006 | Iizuka et al. | |
| 2008/0166326 A1 | 7/2008 | Lowdell | |
| 2009/0068141 A1 | 3/2009 | Parkhurst et al. | |
| 2009/0104170 A1 | 4/2009 | Childs et al. | |
| 2010/0322898 A1 | 12/2010 | Nelson et al. | |
| 2011/0135687 A1 | 6/2011 | Koelle et al. | |
| 2012/0121544 A1 | 5/2012 | Choi et al. | |
| 2013/0059379 A1 | 3/2013 | Schmidt-Wolf | |
| 2013/0287688 A1 | 10/2013 | Jain et al. | |
| 2014/0017713 A1 | 1/2014 | Lee et al. | |
| 2014/0023626 A1 | 1/2014 | Pelled et al. | |
| 2014/0080148 A1 | 3/2014 | Spanholtz | |
| 2014/0120072 A1 | 5/2014 | Yonemitsu et al. | |
| 2014/0286898 A1 | 9/2014 | Gavin et al. | |
| 2014/0369955 A1 | 12/2014 | Markovic et al. | |
| 2014/0369977 A1 | 12/2014 | Zhang et al. | |
| 2015/0118207 A1 | 4/2015 | Min et al. | |
| 2015/0139943 A1 | 5/2015 | Campana et al. | |
| 2015/0152387 A1 | 6/2015 | Lee et al. | |
| 2016/0068584 A1 | 3/2016 | Bechard et al. | |
| 2016/0229901 A1 | 8/2016 | Merchant | |
| 2016/0297821 A1 | 10/2016 | Stefinovic et al. | |
| 2016/0324964 A1 | 11/2016 | Markovic et al. | |
| 2017/0002322 A1 | 1/2017 | Hariri et al. | |
| 2017/0107490 A1 | 4/2017 | Maeurer | |
| 2017/0121673 A1 | 5/2017 | Wolpe | |
| 2017/0240859 A1 | 8/2017 | Yamano et al. | |
| 2017/0349880 A1 | 12/2017 | Doucey et al. | |
| 2018/0010087 A1 | 1/2018 | Miltenyi et al. | |
| 2018/0015123 A1 | 1/2018 | Choi et al. | |
| 2018/0021378 A1 | 1/2018 | Kang et al. | |
| 2018/0057795 A1 | 3/2018 | Childs et al. | |
| 2018/0155690 A1 | 6/2018 | Park et al. | |
| 2018/0161371 A1 | 6/2018 | O'Dwyer | |
| 2018/0223257 A1 | 8/2018 | Lee et al. | |
| 2018/0245044 A1 | 8/2018 | Granzin et al. | |
| 2018/0291341 A1 | 10/2018 | Molleryd et al. | |
| 2018/0371093 A1 | 12/2018 | Bilic et al. | |
| 2019/0112577 A1 | 4/2019 | Wu et al. | |
| 2019/0153389 A1 | 5/2019 | Ffischkoff et al. | |
| 2019/0169276 A1 | 6/2019 | Novak et al. | |
| 2019/0309070 A1 | 10/2019 | Copik et al. | |
| 2019/0314412 A1 | 10/2019 | Copik et al. | |
| 2019/0330592 A1 | 10/2019 | Hariri et al. | |
| 2019/0345449 A1 | 11/2019 | Park et al. | |
| 2020/0095543 A1 | 3/2020 | BhattacharyA et al. | |
| 2020/0108096 A1 | 4/2020 | Min et al. | |
| 2020/0172869 A1 | 6/2020 | Park et al. | |
| 2020/0181220 A1 | 6/2020 | Ptacin et al. | |
| 2020/0188484 A1 | 6/2020 | Ptacin et al. | |
| 2020/0246179 A1 | 8/2020 | Peyman | |
| 2020/0392177 A1 | 12/2020 | Martinez Botella et al. | |
| 2021/0032597 A1 | 2/2021 | Park et al. | |
| 2021/0228640 A1 | 7/2021 | Lu et al. | |
| 2022/0249564 A1 | 8/2022 | Yu et al. | |
| 2023/0002731 A1 | 1/2023 | Park et al. | |
| 2025/0059510 A1 | 2/2025 | Park et al. | |
| 2025/0195574 A1 | 6/2025 | Song et al. | |
| 2025/0255903 A1 | 8/2025 | Song et al. | |
| 2026/0048083 A1 | 2/2026 | Song et al. | |

FOREIGN PATENT DOCUMENTS

| | | | | |
|---|---|---|---|---|
| CN | 105524880 | | 4/2016 | |
| CN | 105524880 A | | 4/2016 | |
| CN | 107922925 A | | 4/2018 | |
| CN | 107970258 | | 5/2018 | |
| CN | 104321425 | | 8/2018 | |
| CN | 114929249 | | 8/2022 | |
| EP | 409655 | | 1/1991 | |
| EP | 248642 | | 10/1992 | |
| EP | 1941027 | | 8/2014 | |
| EP | 2401364 | | 4/2015 | |
| EP | 2923208 | | 9/2015 | |
| EP | 1899459 | | 3/2016 | |
| EP | 2878666 | | 5/2017 | |
| EP | 2142642 | | 8/2017 | |
| EP | 2794859 | | 9/2017 | |
| EP | 3057986 | | 12/2017 | |
| EP | 2593542 | | 1/2018 | |
| EP | 2841563 | | 6/2019 | |
| EP | 2411507 | | 9/2019 | |
| EP | 2725100 | | 9/2019 | |
| EP | 2812011 | | 1/2020 | |
| EP | 2881462 | | 5/2020 | |
| EP | 3656851 | | 5/2020 | |
| EP | 2947144 | | 9/2020 | |
| EP | 3344759 | | 10/2020 | |
| JP | 2015-502756 | | 1/2015 | |
| JP | 2016008198 A | | 1/2016 | |
| JP | 2017-508479 | | 3/2017 | |
| JP | 2017-515506 | | 6/2017 | |
| KR | 10-2012-0016427 | * | 2/2012 | |
| KR | 10-2010007877 | | 2/2012 | |
| KR | 10-2018-0012938 A | | 2/2018 | |
| KR | 10-2018-0012942 A | | 2/2018 | |
| KR | 10-2019-0093499 | | 8/2019 | |
| KR | 10-2019-0093500 | | 8/2019 | |
| RU | 2394561 | | 12/2008 | |
| TW | I439275 B | | 6/2014 | |
| WO | WO 1990/009798 | | 9/1990 | |
| WO | 00/00587 A1 | | 1/2000 | |
| WO | 2004/011673 A1 | | 2/2004 | |
| WO | WO-2006050270 A2 * | | 5/2006 | A61P 15/00 |
| WO | 2006/058248 A2 | | 6/2006 | |
| WO | WO 2008/118369 A2 | | 10/2008 | |
| WO | WO 2010/013947 | | 2/2010 | |
| WO | 2012/009422 A1 | | 1/2012 | |
| WO | 2013/168978 A1 | | 11/2013 | |
| WO | WO 2014/005072 | | 1/2014 | |
| WO | WO 2014/123879 | | 8/2014 | |
| WO | WO 2015/125113 | | 8/2015 | |
| WO | WO 2015/132415 | | 9/2015 | |
| WO | WO 2015/154012 A1 | | 10/2015 | |
| WO | 2016/096903 A1 | | 6/2016 | |
| WO | WO 2016/122147 | | 8/2016 | |
| WO | WO 2016/209021 | | 12/2016 | |
| WO | WO 2017/037083 A1 | | 3/2017 | |
| WO | WO 2017/188790 | | 11/2017 | |
| WO | WO 2017/196657 | | 11/2017 | |
| WO | 2018/118907 A1 | | 6/2018 | |
| WO | WO 2018/161026 A1 | | 9/2018 | |
| WO | WO 2018/194215 | | 10/2018 | |
| WO | WO 2019/014684 | | 1/2019 | |
| WO | WO 2019/046444 | | 3/2019 | |
| WO | WO 2019/152663 | | 8/2019 | |
| WO | WO 2019/165097 | | 8/2019 | |
| WO | WO 2019/168222 | | 9/2019 | |
| WO | WO 2019/175802 | | 9/2019 | |
| WO | WO 2019/182392 | | 9/2019 | |
| WO | WO 2019/213610 | | 11/2019 | |
| WO | WO 2019/229109 | | 12/2019 | |
| WO | WO 2020/006139 | | 1/2020 | |
| WO | WO 2020/095058 | | 5/2020 | |
| WO | WO 2020/101361 | | 5/2020 | |
| WO | WO 2020/103777 | | 5/2020 | |
| WO | WO 2020/104676 | | 5/2020 | |
| WO | WO 2020/112493 | | 6/2020 | |
| WO | WO 2020/112563 | | 6/2020 | |
| WO | WO 2020/146221 | | 7/2020 | |
| WO | WO 2020/172328 | | 8/2020 | |
| WO | WO 2020/187340 | | 9/2020 | |
| WO | WO 2020/205359 | | 10/2020 | |
| WO | WO 2021/108389 | | 6/2021 | |
| WO | WO 2023/235806 | | 12/2023 | |

(56) References Cited

OTHER PUBLICATIONS

Granzin et al., "Fully automated expansion and activation of clinical-grade natural killer cells for adoptive immunotherapy", Cytotherapy 2015; 17:621-32.

Granzin et al., "Highly efficient IL-21 and feeder cell-driven ex vivo expansion of human NK cells with therapeutic activity in a xeno-graft mouse model of melanoma", Oncoimmunology 2016, vol. 5, No. 9 in 11 pages.

Granzin, M. et al., Shaping of Natural Killer Cell Antitumor Activity by Ex Vivo Cultivation, Front. Immunol. 2017, vol. 8:458, pp. 1-18.

Habib et al., IL-21: A novel IL-2-family lymphokine that modulates B, T, and natural killer cell responses, Molecular mechanisms in allergy and clinical immunology, pp. 1033-1044, 2003.

Iyengar et al., "Purification of Human Natural Killer Cells Using a Clinical-Scale Immunomagnetic Method", International Society for Cellular Therapy, Cytotherapy, vol. 5, No. 6, 2003, 479-484.

Jinushi, M., et al., Impairment of natural killer cell and dendritic cell functions by the soluble form of MHC class I-related chain A in advanced human hepatocellular carcinomas, Journal of Hepatology, vol. 43, No. 6, pp. 1013-1020, 2005.

Kim et al., A Phase I/IIa Randomized Trial Evaluating the Safety and Efficacy of SNK01 Plus Pembrolizumab in Patients with Stage IV Non-Small Cell Lung Cancer, Cancer Research and Treatment, 2021.

Klingemann et al., "Ex vivo expansion of natural killer cells for clinical applications", Cytotherapy 2004; 6:15-22.

Kloess et al., "Optimization of human NK cell manufacturing: Fully-automated separation, improved ex vivo expansion using IL-21 with autologous feeder cells and generation of anti-CD123-CAR-expressing effector cells", Human Gene Therapy, Mary Ann Liebert, Inc,, 2017, in 43 pages.

Koehl et al., "IL-2 activated NK cell immunotherapy of three children after haploidentical stem cell transplantation", Blood Cells Mol Dis 2004; 33:261-6.

Koehl, U. et al., Clinical grade purification and expansion of NK cell products for an optimized manufacturing protocol, Front. Oncol. 2013, vol. 3: Oncol. 2013, vol. 3: 118, pp. 1-12.

Lang et al., "Clinical Scale Isolation of T Cell-depleted CD56+ Donor Lymphocytes in Children", Bone Marrow Transplantation (2002) 29, 497-502, in 6 pages.

Lim et al., Effect of exposure to interleukin-21 at various time points on human natural killer cell culture. Cytotherapy, 16:1419-1431 (2014).

Lim, A. L., et al., Ex Vivo Expansion of Highly Cytotoxic Human NK Cells by Cocultivation with Irradiated Tumor Cells for Adoptive Immunotherapy, Therapeutics, Targets, and Chemical Biology, Cancer Research, vol. 73, No. 8, 2013.

Loza et al., The IL-12 signature: NK cell terminal CD56+high stage and effector functions. Journal of Immunology, vol. 172, No. 88-96. 2004.

Miller et al., "Successful Adoptive Transfer and in Vivo Expansion of Human Haploidentical NK Calls in Cancer Patients", American Society of Hematology, 2005 in 33 pages.

Miller., Low Dose Subcutaneous Interleukin-2 After Autologous Transplantation Generates Sustained In Vivo Natural Killer Cell Activity, Biology of Blood and Marrow Transplantation, vol. 3, No. 1, pp. 34-44, 1997.

Mocchegiani, E., et al. Role of zinc and α2macroglobulin on thymic endocrine activity and on peripheral immune efficiency (natural killer activity and interleukin 2) in cervical carcinoma. Br Journal of Cancer, No. 79, pp. 244-250, 1999.

MojoSort(TM) Human NK Cell Isolation Kit, Biolegend, Apr. 18, 2016, [retrieved on Dec. 22, 2020].

Mrozek, E., et al., Role of Interleukin-15 in the Development of Human CD56' Natural Killer Cells From CD34+ Hematopoietic Progenitor Cells, Rapid Communication, Blood, vol. 87, No. 7, pp. 2632-2640, 1996.

Non-Final Office Action received in U.S. Appl. No. 16/773,888 dated Mar. 30, 2020 in 9 pages.

Notice of Allowance mailed Dec. 20, 2019, in U.S. Appl. No. 16/523,964 in 8 pages.

Notice of Allowance mailed Jul. 28, 2020, in U.S. Appl. No. 16/773,888 in 9 pages.

Office Action Dated Apr. 8, 2021 in EP Application No. 19746979.4 in 1 page.

Office Action Dated Dec. 23, 2020 in Japanese Application No. 2020-541915 in 10 pages.

Office Action in Australian Application No. 2019215034, dated Aug. 12, 2020.

Office Action received in Russian Application No. 2020128764 dated Jan. 20, 2021.

Office Action with English Translation dated Dec. 22, 2021 in Iranian Application No. 139950140003004045 in 14 pages.

Office Action with English Translation Dated Dec. 23, 2021 in Saudi Arabian Patent Application No. 520412566 in 6 pages.

Office Action with English Translation Dated Feb. 10, 2022 in European Patent Application No. 19746979.4 in 18 pages.

Office Action with English Translation Dated Jan. 7, 2022 in Chinese Patent Application No. 201980011279.4 in 10 pages.

Office Action with English Translation in Iranian Application No. 139950140003004045 in 12 pages, dated May 24, 2021.

Office Action with English Translation in Japanese Patent Application No. 2020-541915 in 13 pages dated Jun. 8, 2021.

Office Action with English Translation in Russian Application No. 2020128764/10(051457) in 12 paged, dated Apr. 14, 2021.

Office Action with English Translation in Russian Application No. 2020128764/10(051457), dated Oct. 12, 2021.

Ogasawara, K. et al. Requirement for I RF-1 in the microenvironment supporting development of natural killer cells, Nature, vol. 391, pp. 700-703, 1998.

Park et al., "Gene expression analysis of ex vivo expanded and freshly isolated NK cells from cancer patients", J Immunother 33(9): 945-955 (2010).

Parrish-Novak, J., et al. Interleukin 21 and its receptor are involved in NK cell expansion and regulation of lymphocyte function, Nature, vol. 408, 57-63, 2000.

Passweg et al., "Purified donor NK-lymphocyte infusion to consolidate engraftment after haploidentical stem cell transplantation" Nature Publishing Group, Leukemia 18, 2004, 1835-1838.

Patent examination report dated Sep. 29, 2020 in New Zealand Application No. 766453.

Response to First Action Interview Office Action filed Oct. 23, 2019, in U.S. Appl. No. 16/523,964 in 12 pages.

Roseneberg al., "Natural Killer Cells Plus IL-2 Following Chemotherapy to Treat Advanced Melanoma or Kidney Cancer" ClinicalTrials. gov: NCT00328861, May 22, 2006 in 10 pages.

Shibuya A. et al., Lymphokine Requirement for the Generation of Natural Killer Cells From CD34+ Hematopoietic Progenitor Cells, Blood, vol. 85, pp. 3538-3546, 1995.

Smyth. New Aspects of Natural-Killer-Cell Surveillance and Therapy of Cancer, Nature Reviews Cancer, vol. 2, No. 11, pp. 850-861, 2002.

Strengell et al., IL-21 in Synergy with IL-15 or IL-18 Enhances IFN-y Production in Human NK and T Cells, Journal of Immunology, vol. 170, pp. 5464-5469, 2003.

Supplementary European Search Report completed Mar. 10, 2021 received in European Application No. 19746979 in 287 pages.

Tajima, F., et al., Natural Killer Cell Activity and Cytokine Production a Prognostic Factors in Adult Acute Leukemia, Leukemia, vol. 10m pp. 478-482, 1996.

Takaki, R., et al., IL-21 Enhances Tumor Rejection through a NKG2D-Dependent Mechanism, Journal of Immunology, vol. 175, No. 4, pp. 2167-2173, 2005.

Wendt et al., "Interleukin-21 Differentially Affects Human Natural Killer Cell Subsets", The Authors Journal compilation, 2007 Blackwell Publishing Ltd, Immunology, 122, 486-495.

Xiaomei, L. et al., Expansion of NK cells from PBMCs using immobilized 4-1 BBL and interleukin-21, International Journal of Oncology, vol. 47, No. 1, pp. 335-342, 2015.

Non-Final Office Action received in U.S. Appl. No. 14/399,371 dated Aug. 11, 2017 in 9 pages.

(56)　　　　　References Cited

OTHER PUBLICATIONS

International Search Report and Written Opinion mailed on Feb. 12, 2021 for International Patent Application No. PCT/US2020/061984 in 22 pages.
Office Action dated Mar. 10, 2022 received in European Application No. 19746979 in 18 pages.
Office Action with English Summary dated Aug. 23, 2022 in Malaysian Application No. PI2020003935 in 4 pages.
Korean Application with English Translation filed May 7, 2013, in Korean Application No. 10-2013-051442 in 66 pages.
Korean Application with English Translation filed May 7, 2012, in Korean Application No. 10-2012-0048165 in 50 pages.
Lehmann, C. et al., Activation of natural killer cells with interleukin 2 (IL-2) and IL-12 increases perforin binding and subsequent lysis of tumour cells, British Journal of Haematology, vol. 114, 660-665, 2001.
Office Action with English Translation in Indonesia Patent Application No. P-00202006013, dated May 12, 2022.
Notice of Acceptance with English Translation in Indonesia Patent Application No. P-00202006013, dated Jun. 19, 2023.
Office Action with English Translation in Japanese Patent Application No. 2020-541915, dated Oct. 26, 2022.
Office Action with English Translation in Iran Patent application No. 139950140003010289, dated Dec. 12, 2022.
Office Action in Malaysian Application No. PI2020003935, dated Dec. 7, 2022.
Office Action with English Translation in Egyptian Patent Application No. 1112/2020 D1, dated Jan. 18, 2023.
Office Action with English Translation in Japanese Patent Application No. 2021-165698, dated Jan. 31, 2023.
Office Action in U.S. Appl. No. 17/009,558 Dated Mar. 27, 2023.
Office Action with English Translation in Egyptian Patent Application No. 1112/2020, dated Apr. 10, 2023.
Office Action and Search Report in Malaysia Application No. PI2020003935 dated Aug. 23, 2022.
Office Action in Indian Application No. 202017036642 dated May 18, 2023.
Modified Substantive Examination Adverse Report (Section 30(20)) and Search Report in Malaysian Application No. PI2021005196 dated May 24, 2023.
Office Action in Phillipine Application No. 1-2020-551151 dated Jul. 17, 2023.
Office Action with English Translation in Vienamese Application No. 1-2020-04880 dated Jun. 22, 2023.
Office Action with English Translation in Ukrainian Application No. a 2020 05595 dated Apr. 11, 2023.
Chan et.al, The Changing Role of Natural Killer Cells in Cancer Metastasis, The Journal of Clinical Investigation, 2022, vol. 132, No. 6, pp. 1-9.
Notice of Allowance mailed Jul. 16, 2020, in Mexican Application No. MX/a/2020/008039 in 2 pages.
Notice of Allowance with English Translation in Japanese Application No. 2021-165698, dated Jul. 14, 2023.
Notice of Allowance in U.S. Appl. No. 17/009,558, dated Oct. 17, 2023 in 13 pages.
Office Action received in Philippine Patent Application No. 1-2020-551151, dated Nov. 16, 2023.
Office Action with English Summary dated Aug. 22, 2023 in Bangkok—Patent application No. 2001004285.
Office Action with English Summary dated Sep. 12, 2023 in Saudi Arabia—Patent application No. 520420878.
Office Action with English Summary received Iran Patent Application No. 140150140003000836, dated Dec. 12, 2023.
Office Action with English Translation in Iran Patent application No. 139950140003010289, dated Jan. 13, 2023.
Chantal Reina-Ortiz, Expanded NK Cells From Umbilical Cord Blood and Adult Peripheral Blood Combined With Daratumumab Are Effective Against Tumor Cells From Multiple Myeloma Patients, OncoImmunology, Jan. 2021, vol. 10, No. 1, pp. 1853314.

Corrected Notice of Allowability received in U.S. Appl. No. 17/009,558, dated Aug. 26, 2024, in 3 pages.
Corrected Notice of Allowability received in U.S. Appl. No. 17/009,558, dated Aug. 7, 2024, in 3 pages.
De Rham, Casimir, et al., The Proinflammatory Cytokines IL-2, IL-15 and IL-21 Modulate the Repertoire of Mature Human Natural Killer Cell Receptors, Arthritis Research & Therapy 2007, 9:R125.
Extended European Search Report, received in European Patent Application No. 20892302.9, dated Jan. 3, 2024.
File History of U.S. Appl. No. 16/773,888, filed Sep. 1, 2020.
Final Office Action received in U.S. Appl. No. 14/399,371 dated Jan. 25, 2017 in 15 pages.
First Examination Report, received in Australian Patent Application No. 2021266198, dated Feb. 27, 2024.
First Substantive Examination Report, received in United Arab Emirates Patent Application No. P6001104/2020, dated Dec. 20, 2023.
Hui Xu, et al. Single-Cell RNA Sequencing of Peripheral Blood Reveals Immune Cell Signatures in Alzheimer's Disease, Frontiers in Immunology, Aug. 2021, vol. 12, pp. 1-12.
International Preliminary Report on Patentability, received in PCT Application No. PCT/US2020/061984, dated May 17, 2022, in 11 pages.
Krause, S., et al., Treatment of Colon and Lung Cancer Patients with ex Vivo Heat Shock Protein 70-Peptide-Activated, Autologous Natural Killer Cells: A Clinical Phase I Trial, Clinical Cancer Research, vol. 10, 3699-3707, Jun. 1, 2024.
Mao Lin, et al. Pembrolizumab Plus Allogeneic NK Cells in Advanced Non-Small Cell Lung Cancer Patients, The Journal of Clinical Investigation, 2020; vol. 130, No. 5, pp. 2560-2569.
Non-Final Office Action received in Application No. 201380028253.3 dated Mar. 28, 2017.
Notice of Allowance Dated Jul. 28, 2020 in U.S. Appl. No. 16/773,888 in 9 pages.
Notice of Allowance received in U.S. Appl. No. 17/009,558, dated May 24, 2024, in 11 pages.
Notice of Allowance received in U.S. Appl. No. 17/009,558, dated Feb. 5, 2024, in 8 pages.
Notice of Preliminary Rejection, received in Korean Patent Application No. 10-2019-0001981, dated Jan. 11, 2024.
Notice of Preliminary Rejection, received in Korean Patent Application No. 10-2019-0001983, dated Jan. 19, 2024.
Office Action Dated Apr. 1, 2021 in New Zealand Application No. 766453 in 3 pages.
Office Action Dated Aug. 13, 2021 in New Zealand Application No. 766453 in 4 pages.
Office Action Dated Dec. 23, 2020 in Japanese Application No. 2020-541915 in 1 O pages.
Office Action Dated Feb. 22, 2022 in New Zealand Application No. 766453 in 3 pages.
Office Action Dated Mar. 30, 2020 in U.S. Appl. No. 16/773,888 in 9 pages.
Office Action in Korean Patent Application No. 10-2019-7021322 Dated Mar. 17, 2023.
Office Action received in European Patent Application No. 19746979. 4, dated Jun. 20, 2024, in 20 pages.
Office Action received in Australian application No. 2019/215034 dated Aug. 12, 2020, in 3 pages.
Office Action received in Ukrainian Patent Application No. PI2020003935, dated Sep. 12, 2024, in 15 pages.
Sainiteesh Maddineni, et al. Emerging NK Cell Therapies for Cancer and the Promise of Next Generation Engineering of IPSC-Derived NK Cells, Journal for Immuno Therapy of Cancer, May 17, 2022, vol. 10, No. 5.
Second Examination Report, received in Egypt Patent Application No. 1112/2020 D1, dated Mar. 27, 2024.
Second Substantive Examination Report, received in Egypt Patent Application No. 1112/2020, dated Jan. 30, 2024.
Tran, et al., TGFI3R1 Blockade with Galunisertib (LY2157299) Enhances Anti-Neuroblastoma Activity of Anti-GD2 Antibody Dinutuximab (ch14.18) with Natural Killer Cells, Clin Cancer Res. Oct. 10, 2016. pii: clincanres.1743.2016.

(56) References Cited

OTHER PUBLICATIONS

Walewski, J. et al., Evaluation of natural killer and lymphokine-activated killer (LAK) cell activity in vivo in patients treated with high-dose interleukin-2 and adoptive transfer of autologous LAK cells, Journal of Cancer Research Clinical Oncology, (1989) 114_ 170-174.

Written Opinion, received in Singapore Patent Application No. 11202205535X, dated Feb. 29, 2024.

Ye Li, et al. Human IPSC-Derived Natural Killer Cells Engineered With Chimeric Antigen Receptors Enhance Antitumor Activity, Cell Stem Cell, Aug. 2, 2018, pp. 181-182.

Chen et al., Development and dynamics of robust T-cell responses to CML under imatinib treatment, Blood. Jun. 1, 2008;111(11):5342-9.

Chinese Office Action dated Mar. 28, 2017 in Application No. 201380028253.3, 6 pages.

Egyptian Office Action in Patent Application No. 1112/2020 dated Oct. 28, 2024 in 12 pages.

Hassold et al., Enhancement of natural killer cell effector functions against selected lymphoma and leukemia cell lines by dasatinib, Int J Cancer. Sep. 15, 2012;131(6): E916-27.

International Preliminary Report on Patentability received for PCT Patent Application No. PCT/KR2013/003981, mailed on Nov. 20, 2014, 15 pages (9 pages of English Translation and 6 pages of Original Document).

International Preliminary Report on Patentability received for PCT Patent Application No. PCT/US2017/067289, mailed on Jul. 4, 2019, 7 pages.

International Preliminary Report on Patentability received for PCT Patent Application No. PCT/US2019/016076, mailed on Aug. 13, 2020, 7 pages.

International Search Report and Written Opinion received for PCT Patent Application No. PCT/US2017/067289, mailed on Mar. 1, 2018, 8 pages.

Iranian Office Action dated Dec. 12, 2023 in Application No. 140150140003000836, 13 pages.

Iranian Office Action in Iranian Application No. 139950140003004045, dated Dec. 22, 2021 in 14 pages.

Kaneko et al., A report of three patients treated with immunocell therapy with imatinib mesylate, Anticancer Res. Sep.-Oct. 2004;24(5C):3303-3309.

Koelle, D. M., et al., "Herpes simplex virus infection of human fibroblasts and keratinocytes inhibits recognition by cloned CD8+ cytotoxic T lymphocytes," J. Clin. Invest., vol. 91, 1993, pp. 961-968.

Lee et al, "Histone deacetylase inhibitor, CG200745, attenuates cardiac hypertrophy and fibrosis in COCA-induced nypertensive rats", Korean J Physiol Pharmacol, vol. 20 No. 5, p. 477-485, (2016).

Lee et al, "A randomized, multicenter, phase III trial to evaluate the efficacy and safety of Polmacoxib compared with Celecoxib and placebo for patients with Osteoarthritis"; Clin Ortho Surg. Dec. 1, 2017; 9(4): 439-457.

Min et al., Optimization of large-scale expansion and cryopreservation of human natural killer cells for anti-tumor therapy. Immune network. Aug. 21, 2018;18(4):e31; pp. 1-13.

Raj et al., Autologous Immune Enhancement Therapy in Philadelphia Chromosome Positive Acute Lymphoblastic Leukemia, Indian J Hematol Blood Transfus. Sep. 2014;30(Suppl 1):202-4.

Russian Notice of Allowance dated Aug. 1, 2022 in Application No. 2020128764, 15 pages.

U.S. Office Action dated Jul. 10, 2020 in U.S. Appl. No. 15/948,619, 11 pages.

U.S. Office Action Dated Oct. 22, 2021 in U.S. Appl. No. 16/471,548 in 10 pages.

U.S. Office Action in U.S. Appl. No. 16/471,548 dated Mar. 11, 2022 in 10 pages.

File History of U.S. Appl. No. 17/009,558, filed Sep. 1, 2020.

International Search Report and Written Opinion, received in PCT Application No. PCT/US2023/067766, dated Oct. 17, 2023, in 14 pages.

International Search Report and Written Opinion, received in PCT Application No. PCT/US2023/070004, dated Nov. 29, 2023, in 17 pages.

International Search Report and Written Opinion, received in PCT Application No. PCT/US2023/070005, dated Dec. 8, 2023, in 19 pages.

International Search Report and Written Opinion, received in PCT Application No. PCT/US2023/071954, dated Jan. 2, 2024, in 18 pages.

International Search Report and Written Opinion, received in PCT Application No. PCT/US2023/080167, dated Apr. 19, 2024, in 18 pages.

Lim Dong-Pyo, et al. Effect of Exposure to Interleukin-21 at Various Time Points on Human Natural Killer Cell Culture, Cytotherapy, vol. 16, No. 10, Oct. 1, 2024, pp. 1419-1430.

Lim et al., GMP-Compliant, large scale expanded allogenic natural killer cells have potent cytolytic activity against cancer cells in vitro and in in vivo, PLoS One, Jan. 2013, vol. 8, No. 1, E53611, pp. 1-9.

Office Action in Philippines Application No. 1-2020-551151 dated Jul. 17, 2023.

Office Action received in Australian Patent Application No. 2021266198, dated Oct. 29, 2024, in 4 pages.

Office Action received in Australian Patent Application No. 2021266198, dated Aug. 9, 2024, in 4 pages.

Office Action received in Taiwan Patent Application No. 109141339, dated Jul. 31, 2024, in 41 pages.

Office Action received in Taiwan Patent Application No. 109141339, dated Jan. 21, 2025, in 7 pages.

Office Action English Summary dated Aug. 23, 2022 in Malaysian Application No. PI2020003935 in 4 pages.

Office Action with English Summary dated Aug. 29, 2022 in Saudi Arabia—Patent application No. 520420878.

Office Action with English Summary dated Oct. 10, 2024 in Japanese Application No. 2023-136268 in 11 pages.

Office Action with English Translation dated Oct. 11, 2024 in Chilean Patent Application No. 202002011, in 5 pages.

Office Action with English Translation Dated Oct. 28, 2024 in Egypt Patent Application No. 1112/2020 in 12 pages.

Office Action with English translation dated Sep. 15, 2024 in Saudi Arabia—Patent application No. 520420878 in 9 pages.

Office Action with English Translation in Chilean Patent Application No. 202002011, dated Feb. 8, 2022.

Office Action with English Translation in Chilean Patent Application No. 202002011, dated Jul. 25, 2022.

Office Action with English Translation received in Korean Application No. 10-2019-0001983 dated Sep. 25, 2024 in 7 pages.

Office Action with English Translation in Japanese Patent Application No. 2022-531631 dated Nov. 22, 2024.

Supplementary European Search Report Dated Mar. 10, 2021 in European Application No. 19746979 in 287 pages.

Apel et al., Integrated clinical scale manufacturing system for cellular products derived by magnetic cell separation, centrifugation and cell culture. Chem Ing Tech. Feb. 2013; 85(1-2):103-110.

Baust et al. Cryopreservation: An emerging paradigm change. Organogenesis. Jul. 2009; 5(3):90-6 (Year: 2009).

India Office Action in Application No 202017036642 dated Aug. 18, 2025 in 3 pages.

Iranian Office Action in Patent Application No. 139950140003010289, dated Apr. 27, 2025; 14 pages.

Japanese Office Action dated May 20, 2025 for Patent Application No. 2022-531631; 14 pages.

Karnieli, Bioreactors and Downstream Processing for Stem Cell Manufacturing; Cryopreservation section; Stem Cell Manufacturing 2016, pp. 141-160 (Year: 2016).

Mexican Office Action dated Jul. 2, 2025 in Application No. MX/a/2021/004682 in 13 pages.

Non-Final Office Action received in U.S. Appl. No. 14/399,371, dated May 16, 2016 in 09 pages.

Non-Final Office Action received in U.S. Appl. No. 16/773,888, dated Mar. 30, 2020 in 06 pages.

(56)                    References Cited

OTHER PUBLICATIONS

Notice of Allowance received in U.S. Appl. No. 14/399,371, dated Feb. 23, 2018 in 08 pages.

Notice of Allowance received in U.S. Appl. No. 16/773,888, dated Jul. 28, 2020 in 08 pages.

Office Action Dated Apr. 2, 2025 in Chilean Patent Application No. 2020-02011 in 3 pages.

Qatar Office Action dated Jun. 25, 2025 for Application No. QA/202007/000404, in 10 pages.

Skak et al., Interleukin-21 activates human natural killer cells and modulates their surface receptor expression. Immunology. Apr. 2008; 123(4):575-583; Epub Nov. 14, 2007.

U.S. Office Action dated Aug. 8, 2025 in U.S. Appl. No. 17/780,204, 8 pages.

Van Acker et al., CD56 in the immune system: more than a marker for cytotoxicity? Frontiers in immunology. Jul. 24, 2017;8:892, 9 pages.

Vietnam Office Action dated Jun. 20, 2025 in Application No. 1-2023-06397 in 3 pages.

Egyptian Office Action, re EG Application No. EG/P/2020/01112, mailed Jan. 28, 2026.

Korean Office Action, re KR Application No. 10-2022-7020872, mailed Mar. 12, 2026.

Mexican Office Action, re MX Application No. MX/A/2021/004682, mailed Feb. 11, 2026.

Australian Notice of Acceptance dated Dec. 10, 2024 in Patent Application No. 2021266198; 4 pages.

Brazil Office Action, re BR Application No. 112020015512.8, mailed Nov. 7, 2025 in 4 pages.

Canadian Office Action dated Sep. 16, 2025 in Application No. 3,089,853; 5 pages.

International Preliminary Report on Patentability for PCT Application No. PCT/US2023/070005, dated Feb. 20, 2025.

International Preliminary Report on Patentability for PCT Application No. PCT/US2024/028934, dated Nov. 27, 2025.

International Search Report and Written Opinion for PCT Application No. PCT/US2024/028934, , dated Aug. 20, 2024.

Japanese Office Action, re JP Application No. 2022-531631, mailed Nov. 4, 2025 in 7 pages.

Notice of Hearing re Indian Application No. POK/Application No /202017036642, dated Sep. 19, 2025.

Ser et al., "Treatment of Alzheimer's disease with the GSK-3 inhibitor tideglusib: a pilot study", Journal of Alzheimer's Disease, vol. 33. Issue 01, Jul. 2012, pp. 205-215.

* cited by examiner

【Figure 1A】
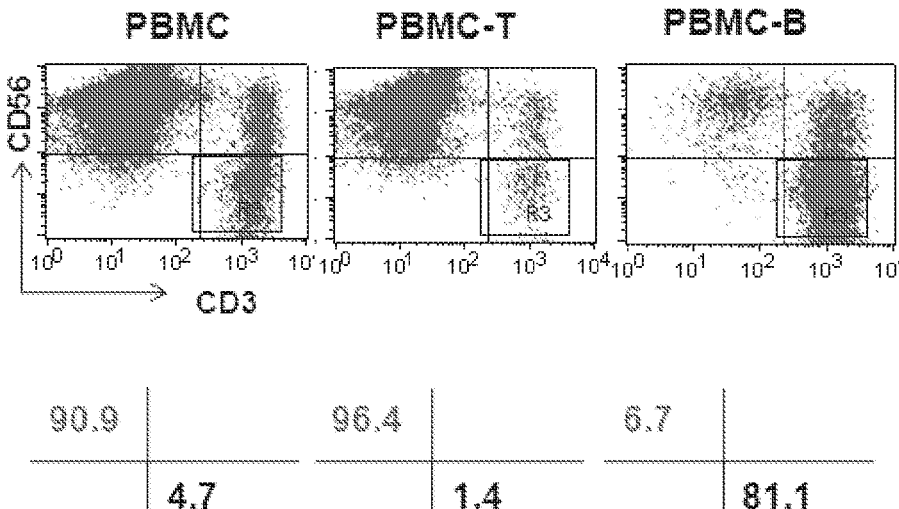
| 90.9 | | 96.4 | | 6.7 | |
|---|---|---|---|---|---|
| | 4.7 | | 1.4 | | 81.1 |
【Figure 1B】
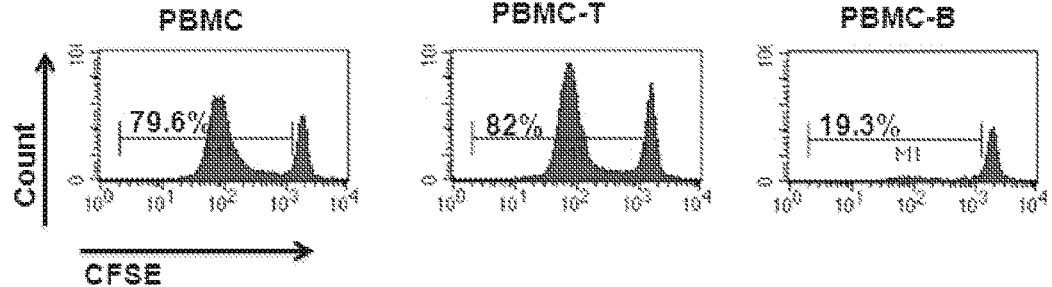

【Figure 2】
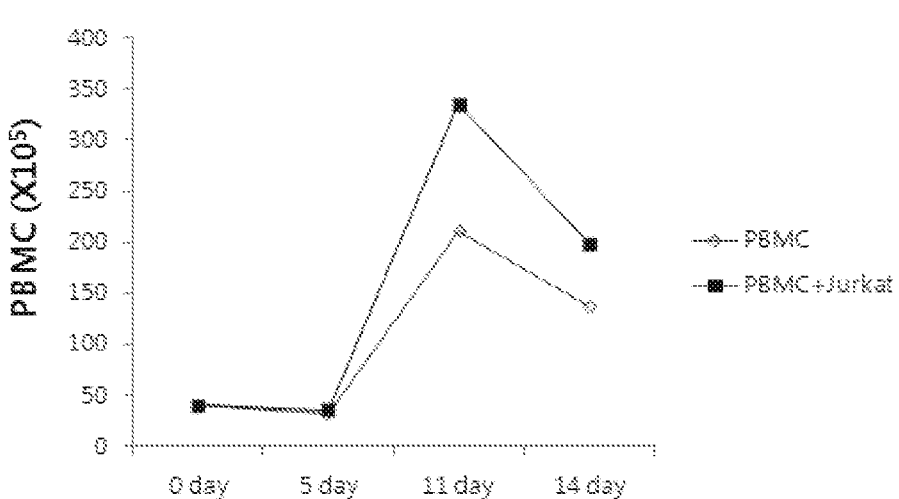
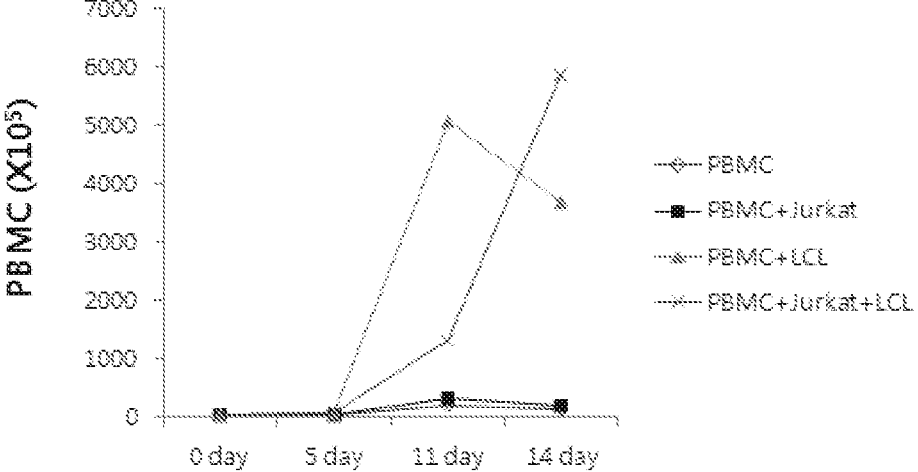

【Figure 3】
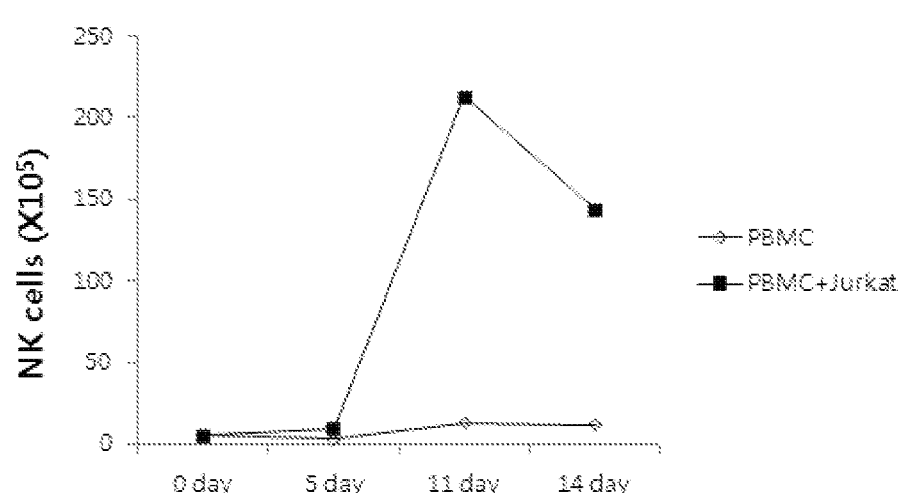
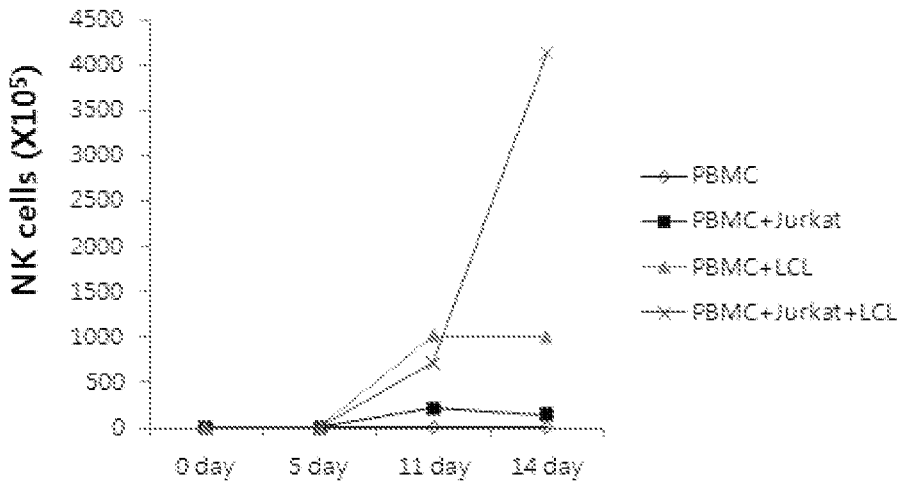

[Figure 4A]
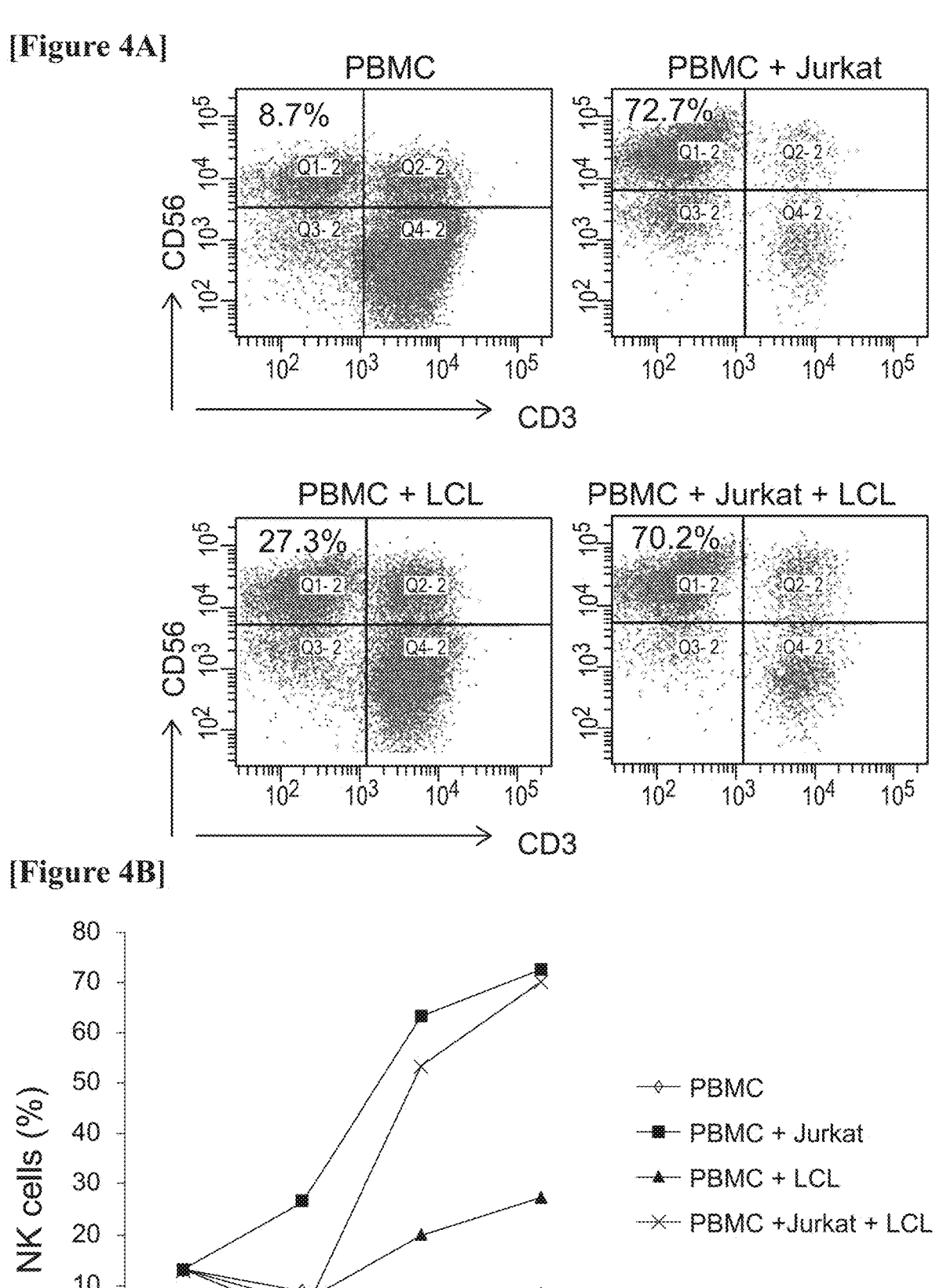
[Figure 4B]

【Figure 5】
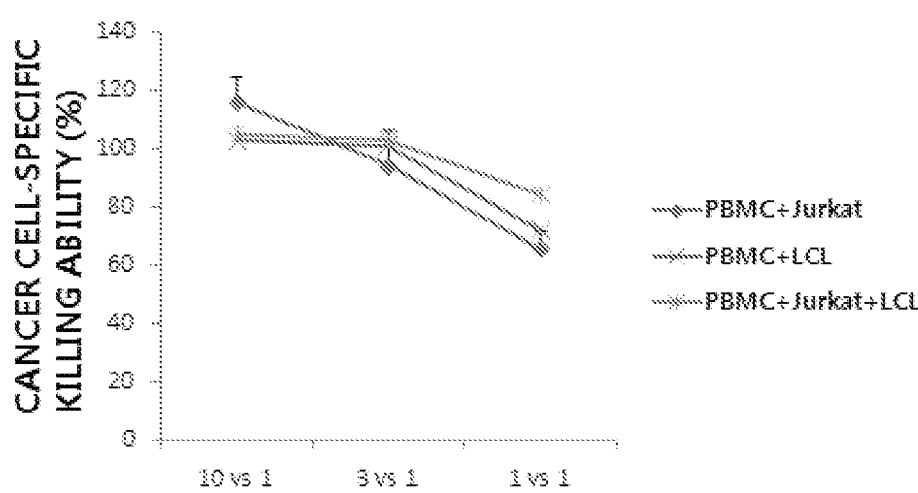
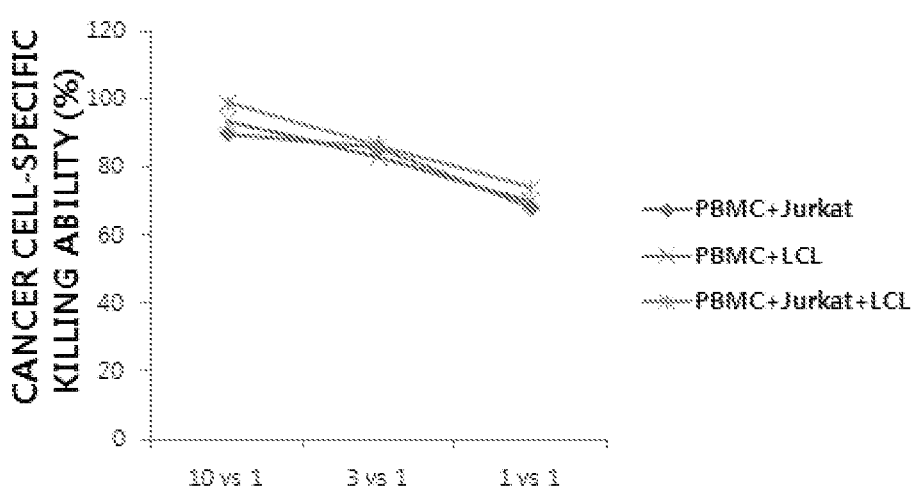

[Figure 6]
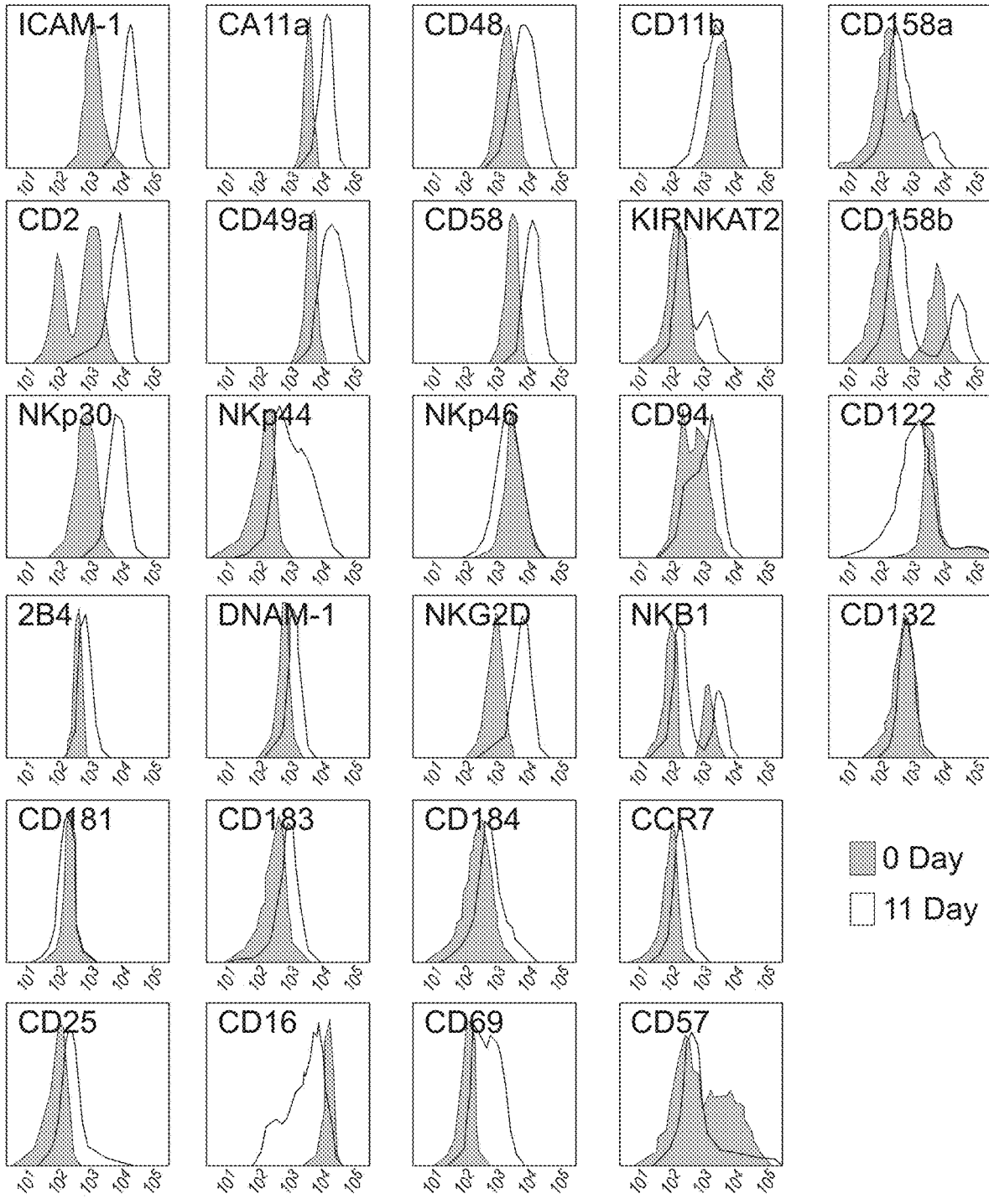

METHOD FOR THE INDUCTION AND EXPANSION OF NATURAL KILLER CELLS DERIVED FROM PERIPHERAL BLOOD MONONUCLEAR CELLS

CROSS-REFERENCE TO RELATED APPLICATIONS

This application is a divisional of U.S. application Ser. No. 14/399,371, filed on Nov. 6, 2014, now U.S. Pat. No. 9,938,498, which is a national stage application, filed under 35 U.S.C. § 371, of International Application No. PCT/KR2013/003981, filed on May 7, 2013, which claims the benefit of, and priority to, Korean Patent Application Nos. 10-2012-0048165, filed on May 7, 2012 and 10-2013-0051442, filed on May 7, 2013.

TECHNICAL FIELD

The present invention relates to a method for inducing and expanding natural killer cells derived from peripheral blood mononuclear cells.

BACKGROUND ART

Immune responses protect a human body from pathogens, and the immune system is composed of many immune-related cells and cytokines. Leukocytes, especially lymphocytes, play an important role in the immune system. Representative examples of cells constituting the lymphocytes include innate immune system cells and acquired immune system cells. Natural killer cells (NK cells) are one of the representative innate immune cells, and known as cells that can kill cancer in a non-specific manner, recognize and kill viruses, bacteria, and the like, and kill pathogens with enzymes such as perforins and granzymes or by Fas-FasL interaction. In the case of cancer patients, a decrease in the ability of such NK cells to kill cancer cells is reported to be deeply associated with the onset of diseases such as lung cancer (Carrega P, et al., Cancer, 2008: 112: 863-875), liver cancer (Jinushi M, et al., J Hepatol., 2005: 43; 1013-1020), breast cancer (Bauernhofer T, et al., Eur J Immunol., 2003: 33: 119-124), uterine cancer (Mocchegiani E., et al., Br j Cancer., 1999: 79: 244-250), blood cancer (Tajima F., et al, Lekemia 1996: 10: 478-482), and the like. Therefore, an increase in the ability and activity of the natural killer cells in regards to killing the cancer cells in cancer patients is essential for cancer treatment. Attempts to treat solid cancer or blood cancer are being currently conducted using such an ability of the NK cells to kill the cancer cells.

To obtain an effect of killing cancer cells, a large quantity of NK cells are needed, but it is difficult to ensure obtaining a large amount of blood from cancer patients, and the NK cells in the blood merely amount to a proportion of approximately 5 to 20%. Thus, since it is difficult to use the NK cells as an immunotherapeutic agent, it is important to extend and proliferate the NK cells effectively. A conventional method of expanding the NK cells typically includes separating or inducing NK cells from bone marrow or mononuclear cells in the blood using an apparatus such as a magnetic activated cell sorter (MACS), cliniMACS, or a fluorescence activated cell sorter (FACS). In such methods, the following operations proceed as follows: 1) separating NK cells from mononuclear cells at early stages and expansion-culturing the NK cells using cytokines; 2) removing T cells coexisting with the mononuclear cells and expansion-culturing the NK cells using cytokines; and 3) inducing the NK cells from stem cells present in the bone marrow. In addition, as the method of isolating NK cells from peripheral blood mononuclear cells (PBMCs) using feeder cells, a method using a RPMI8866 cell line that is derived from B cell leukemia by the Torelli research team from the Republic of Italy, and a method using a HFWT cell line that is derived from a Wilms tumor cell by the Ishikawa research team from Japan have been reported.

However, methods for expanding NK cells reported in the related art are encumbered by the requirement for sophisticated equipment to select cells pre-expansion, the use of genetically engineered feeder cells, and a cocktail of costly cytokines in high concentrations, and thus may be prohibitively expensive for general use, are more difficult to implement and limit accessibility of this approach to the patient population.

DISCLOSURE

Technical Problem

The present invention is directed to providing a novel method for inducing and expanding NK cells derived from peripheral blood, thereby leading to efficient strategy for obtaining activated NK cells derived from peripheral blood without the use of expensive equipment, costly resources or regulatory constraints.

Technical Solution

To solve these problems, one aspect of the present invention provides a method for selectively inducing and expanding NK cells derived from peripheral blood mononuclear cells, which comprises a simplified approach of co-culturing irradiated Jurkat cells and irradiated EBV-LCL cells as feeder cells with the peripheral blood mononuclear cells in the presence of cytokines in defined proportions and concentrations.

Unless specifically stated otherwise, all the technical and scientific terms used in this specification have the same meanings as generally understood by those skilled in the related art to which the present invention belongs. In general, the nomenclature used in this specification and the experimental methods described below are widely known and generally used in the related art.

The present inventors have conducted research to obtain a large quantity of NK cells from a small quantity of blood, and found that the proliferated NK cells can be obtained when mononuclear cells separated from peripheral blood are cultured using irradiated Jurkat cells as feeder cells (Korean Patent Application No. 10-2010-007877).

Also, the present inventors have conducted research on a mechanism in which the NK cells are selectively proliferated using the method disclosed in the patent application, and found that selective proliferation of the NK cells decreases significantly when B cells are removed from mononuclear cells and the mononuclear cells are co-cultured with the irradiated Jurkat cells, indicating that the B cells play an important role in the proliferation of the NK cells (FIGS. 1A and 1B).

Based on these results, it was found that the selective proliferation of the NK cells using the Jurkat cells is dependent on the B cells. From these facts, it was expected that a larger amount of the NK cells can be proliferated when B cell-derived immortalized cells, EBV-LCL, are used as the feeder cells. However, it can be seen that, when the mononuclear cells separated from the peripheral blood are co-cultured with EBV-LCL, the NK cells proliferate, but the purity of the NK cells is significantly lowered. Accordingly, the present inventors have found that all the problems caused when the Jurkat cells or EBV-LCL cells are used alone can be solved when the irradiated EBV-LCL cells are used with the irradiated Jurkat cells as the feeder cells, and the mononuclear cells and NK cells can be proliferated with a much higher yield. Therefore, the present invention has been developed based on these facts.

Therefore, according to one aspect of the present invention, a method for inducing and expanding natural killer cells derived from peripheral blood mononuclear cells is provided, which comprises co-culturing irradiated Jurkat cells and irradiated EBV-LCL cells as feeder cells with peripheral blood mononuclear cells in the presence of cytokines.

In the present invention, the "peripheral blood mononuclear cells," "PBMCs" or "mononuclear cells" refer to mononuclear cells separated from peripheral blood typically used for anti-cancer immunotherapy. The peripheral blood mononuclear cells can be obtained from human blood collected using known methods such as the Ficoll-Hypaque density gradient method.

According to one exemplary embodiment of the present invention, "peripheral blood mononuclear cells" may be obtained from a normal person, a patient at risk of cancer, or a cancer patient. The peripheral blood mononuclear cells used herein do not need to necessarily be autologous, and allogenic peripheral blood mononuclear cells may also be used to induce and proliferate the NK cells for anti-cancer immunotherapy according to the present invention.

When the peripheral blood mononuclear cells are co-cultured with the irradiated Jurkat cells and the irradiated EBV-LCL cells according to one exemplary embodiment of the present invention, the proliferated mononuclear cells and the proliferated natural killer cells may be obtained. A normal person, a patient at risk of cancer, or a cancer patient may be treated with the NK cells thus obtained for prevention and treatment of cancer.

In the present invention, the term "Jurkat cells" or "Jurkat cell line" refers to a blood cancer (immortalized acute T cell leukemia) cell line which has been developed by Dr. Arthur Weiss of the University of California at San Francisco. As cells in which various chemokine receptors are expressed and IL-2 can be produced from the cells, the Jurkat cell line was considered to be a cell line which had no probability as a candidate for the feeder cells (feeder cells) used in anti-cancer immunotherapy since a natural killer cell activation inhibitor, MHC class I, is highly expressed on the cell surface thereof. However, the present inventors have found that many blood cancer cell lines are screened for differentiation of the NK cells from the peripheral blood mononuclear cells and proliferation of the NK cells, and the Jurkat cells are able to be used as the feeder cells (see Korean Patent Application No. 10-2010-0078777). The Jurkat cells used herein may be obtained from the American Type Culture Collection (ATCC; ATCC TIB-152).

In the present invention, the term "EBV-LCL cells" or "EBV-LCL cell line" refers to an Epstein-Barr virus transformed lymphocyte continuous line (EBV-LCL) (D. M. Koelle et al., 1993, supra,). The EBV-LCL cells are often used for research on carcinogenesis, but are not used as the feeder cells to proliferate mononuclear cells and NK cells from the peripheral blood. The EBV-LCL cells according to one exemplary embodiment of the present invention may be directly prepared and used in a typical laboratory. According to one exemplary embodiment of the present invention, the EBV-LCL cells are directly prepared and used. EBV-LCL is a B cell line prepared by transfecting human B cells with an Epstein-Barr virus in vitro. Cyclosporine A is added to suppress T cells reacting to EBV during a procedure of preparing a cell line by transfecting PBMCs with EBV. Specifically, $30 \times 10^6$ PBMCs are added to 9 ml of a culture medium, and the culture medium is placed into a T 25 culture flask. Next, 9 ml of an EBV supernatant is put into the T 25 culture flask. 80 µl of cyclosporine A is then added, and the contents of the flask are cultured at 37° C. After 7 days of culturing, a half of the supernatant is removed, and a fresh culture medium is added. After this, 40 µl of cyclosporine A is added. This procedure is repeatedly performed in the same manner as performed once every 7 days until day 28 of the culture. The cell line may be used after 28 days of the culture. From day 28 on, the cell line is cultured in the culture medium without adding cyclosporine A to the culture medium.

The Jurkat cells and the EBV-LCL cells may be used as the feeder cells even when the Jurkat cells and the EBV-LCL cells are irradiated with radiation to suppress proliferation of cancer cells. According to one exemplary embodiment of the present invention, each of the irradiated Jurkat cells and the irradiated EBV-LCL cells may be obtained by irradiation with radiation of 100 to 500 Gy.

In the present invention, the term "cytokine" refers to an immune activating cytokine that can be used to induce the NK cells from peripheral blood mononuclear cells. According to one exemplary embodiment of the present invention, IL-2, IL-15, IL-21, Flt3-L, SCF, IL-7, IL-12, or IL18 may be used as such a cytokine alone or in combination. In particular, since IL-2, IL-15 or IL-21 is known as a cytokine having an excellent effect in differentiation of the peripheral blood mononuclear cells into the NK cells and proliferation of the NK cells, it is desirable to use these cytokines. According to one exemplary embodiment of the present invention, IL-2 is used, but the present invention is not limited thereto.

The fact that the cytokines are associated with inducement into the NK cells may be found in various documents. From the fact that B cells and T cells are found in mice in which expression of γc of a cytokine receptor does not occur, and NK cells are not found in the mice, cytokine receptors containing γc are known to play an important role in differentiation into the NK cells (Singer, B et al., Proc. Natl. Acad. Sci. USA 92, 377-381, 1995). The γc type of the receptor includes receptors of IL-2, IL-4, IL-7, IL-9, IL-15, and IL-21. Among these, IL-2 is reported to have a function which promotes proliferation and activation of mature NK cells (Shibuya, A. et al., Blood 85, 3538-3546, 1995). It has been reported that the number of the NK cells is significantly lowered in humans and mice which lack IL-2 (DiSanto, J. P. et al., J. Exp. Med. 171, 1697-1704, 1990). On the other hand, there are studies showing that the lack of IL-2 and IL-2Ra indirectly exert an influence on the number and activation of the NK cells. In addition, an IL-2R chain is known to play a part in formation of an IL-15 receptor.

The IL-15 plays a part in differentiation into NK cells. This is found from the fact that the NK cells are lacking in the mice which lack transcription factor interferon (IFN)-regulatory factor 1 required for IL-15 production (Kouetsu et al., Nature 391, 700-703, 1998), and that the NK cells are not found in the mice in which IL-15 or IL-15Rα is lacking. As a result, it has been reported that IL-15 directly promotes growth and differentiation of the NK cells by means of the IL-15 receptor expressed in the NK cells (Mrozek E et al., Blood 87, 2632-2640, 1996).

IL-21 is a cytokine secreted by activated CD4+ T cells (Nature, 5:688-697, 2005), and the IL-21 receptor (IL-21R) is expressed in lymphocytes such as dendritic cells, NK cells, T cells, and B cells (Rayna Takaki, et al., J. Immonol 175: 2167-2173, 2005). IL-21 is structurally highly similar to IL-2 and IL-15, and IL-21R shares a chain with IL-2R, IL-15, IL-7R, and IL-4R (Asao et al., J. Immunol, 167: 1-5, 2001). IL-21 has been reported to induce maturation of an NK cell precursor from bone marrow (Parrish-Novak, et al., Nature, 408: 57-63, 2000), particularly promote effector functions such as an ability of the NK cells to produce cytokines and kill cells (M. Strengell, et al., J Immunol, 170, 5464-5469, 2003; J. Brady, et al., J Immunol, 172, 2048-2058, 2004), and promote the anti-cancer response of the innate and adaptive immune systems by enhancing the effector functions of CD8+ T cells (Rayna Takaki, et al., J Immunol 175, 2167-2173, 2005; A. Moroz, et al., J Immunol, 173, 900-909, 2004). Also, IL-21 has been reported to activate the NK cells separated from human peripheral blood (Parrish-Novak, et al., Nature, 408, 57, 2000), and induce mature NK cells from haematopoietic stem cells separated from cord blood (J. Brady, et al., J Immunol, 172, 2048, 2004).

According to one exemplary embodiment of the present invention, cytokine may be used at a concentration of 50 U/ml to 1,000 U/ml, for example, 200 U/ml to 800 U/ml, or 400 U/ml to 600 U/ml. A conventional method of expanding NK cells requires a high concentration of various cytokines, but in the method of expanding NK cells according to one exemplary embodiment of the present invention, the NK cells may be proliferated with high yield and purity even when one cytokine is used at a low concentration due to the use of two types of feeder cells.

In the present invention, a typical medium may be used without limitation as long as a medium that may be used in the culture of the peripheral blood mononuclear cells can be used to induce the peripheral blood mononuclear cells to become NK cells and proliferate the NK cells. For example, an RPMI, DMEM, x-vivo10, x-vivo20, or cellgro SCGM medium may be used as such a medium. In addition, the culture conditions such as temperature and the like may correspond to the typical culture conditions for the peripheral blood mononuclear cells.

According to one exemplary embodiment of the present invention, the peripheral blood mononuclear cells, the irradiated Jurkat cells and the irradiated EBV-LCL cells may be co-cultured for 7 days to 30 days, for example, 10 days to 20 days. Preferably, the co-culturing is efficiently performed for 10 days to 14 days.

According to another exemplary embodiment of the present invention, when the peripheral blood mononuclear cells are co-cultured with the feeder cells, the peripheral blood mononuclear cells and the feeder cells may be mixed at a mixing ratio of 1:5 to 2:1.

According to one exemplary embodiment of the present invention, to determine an effect of the Jurkat cells and EBV-LCL cells as the feeder cells on inducement and proliferation of the NK cells, four different groups are cultured for a predetermined period of time as follows: a group in which the mononuclear cells are cultured in the presence of IL-2 (control 1), a group in which the mononuclear cells are cultured with the irradiated Jurkat cells in the presence of IL-2 (control 2), a group in which the mononuclear cells are cultured with the irradiated EBV-LCL cell in the presence of IL-2 (control 3), and a group in which the mononuclear cells are co-cultured with the irradiated Jurkat cells and the irradiated EBV-LCL cells in the presence of IL-2 as an experimental group. And, the PBMC and NK cells are then counted (see Example 2, and FIGS. 2 and 3). As a result, it is confirmed that the number of the PBMC increase approximately 147 times more in the experimental group in which the mononuclear cells are co-cultured with the irradiated Jurkat cells and the irradiated EBV-LCL cells in the presence of IL-2 than that in the controls (FIG. 2). In addition to the proliferation of the NK cells, a level of enrichment of the NK cells is also determined. As a result, it is revealed that the ratio of NK cell phenotypes, CD56+ and CD3 cells, increases to 70% or more in the experimental group in which the mononuclear cells are co-cultured with the Jurkat cells and the EBV-LCL cells in the presence of IL-2 after the 14-day culture (FIG. 4A).

Meanwhile, the method of expanding NK cells according to one exemplary embodiment of the present invention may further comprise adding the irradiated Jurkat cells, the irradiated EBV-LCL cells and the cytokines on day 1 to day 15 of a subsequent culture performed to maintain the NK cells after the inducement and proliferation of the NK cells derived from the peripheral blood mononuclear cells. The activated NK cells have a problem in that it is difficult to undergo immunotherapy using the activated NK cells due to their short lifetime. Therefore, the lifetime of the activated NK cells may be extended, and a larger amount of the NK cells may be obtained by adding the irradiated Jurkat cells, the irradiated EBV-LCL and the cytokines on day 1 to day 15 of the culture after the proliferation of the NK cells according to one exemplary embodiment of the present invention.

According to another aspect of the present invention, a composition for preventing and treating cancer including the NK cells derived from the peripheral blood mononuclear cells obtained by the above method, use of the NK cells derived from the peripheral blood mononuclear cells obtained by the method for preparing a medicament for prevention and treatment of cancer, or a method of preventing and treating cancer including administering an effective amount of the NK cells derived from the peripheral blood mononuclear cells obtained by the above method is provided.

According to one exemplary embodiment of the present invention, the NK cells obtained from the group in which the mononuclear cells are co-cultured with the irradiated Jurkat cells in the presence of IL-2 (control 2), the group in which the mononuclear cells are co-cultured with the irradiated EBV-LCL cells in the presence of IL-2 (control 3), and the group in which the mononuclear cells are co-cultured with the irradiated Jurkat cells and the irradiated EBV-LCL cells in the presence of IL-2 (an experimental group) are evaluated for their ability to kill cancer cells. As a result, it is revealed that the NK cells of the experimental group which proliferate approximately 800 higher than the controls have potency that kills cancer cells, which does not weaken.

Therefore, the NK cells obtained by the method according to one exemplary embodiment of the present invention may be effectively used to prevent and treat cancer.

According to one exemplary embodiment of the present invention, the subject may be a human in need of prevention and/or treatment of cancer. A subject may be a patient at risk of cancer, a normal person, or a cancer patient.

The composition for preventing and treating cancer comprising the NK cells derived from the peripheral blood mononuclear cells according to one exemplary embodiment of the present invention may be formulated into preparations in which the NK cells derived from the peripheral blood mononuclear cells are suspended at a proper concentration in an aqueous solution optionally including proper components (for example, a phosphate buffer, a typical aqueous solution for an injection, etc.)

The pharmaceutical composition for preventing and treating cancer according to one exemplary embodiment of the present invention may be administered via a typical route such as an intravenous, intraarterial, intraperitoneal, intramuscular, or intrasternal injection.

An effective amount of the NK cells derived from the peripheral blood mononuclear cells included in the pharmaceutical composition according to one exemplary embodiment of the present invention refers to an amount required to achieve an effect of preventing or treating cancer. Therefore, the effective amount of the NK cells may be adjusted according to the type of a disease, the severity of a disease, the types and contents of other components included in the composition, age, weight, general health conditions and gender of a patient, diet, an administration time, a route of administration, a treatment duration, and various factors including drugs used together with the NK cells. The NK cells derived from the peripheral blood mononuclear cells according to one exemplary embodiment of the present invention may, for example, be administered to an adult at a dose of $1 \times 10^6$ cells/kg to $1 \times 10^{11}$ cells/kg, for example, $1 \times 10^6$ cells/kg to $1 \times 10^8$ cells/kg, when administered once or in divided doses, but the present invention is not limited thereto.

Advantageous Effects

According to the present invention, a large quantity of the NK cells can be induced and proliferated from a small quantity of the peripheral blood mononuclear cells without using expensive equipment or various kinds of expensive cytokines, and thus the NK cells can be used to remarkably improve efficiency and efficacy in preventing and treating cancer.

DESCRIPTION OF DRAWINGS

FIG. 1A shows the results obtained by determining levels of inducement into NK cells after mononuclear cells separated from peripheral blood are co-cultured with Jurkat cell lines (PBMC), PBMCs from which only T cells are removed are co-cultured with the Jurkat cell line (PBMC-T), or PBMCs from which only B cells are removed are co-cultured with the Jurkat cell line (PBMC-B).

FIG. 1B shows that the NK cells do not selectively proliferate when the PBMCs are co-cultured with the Jurkat cell line to proliferate the NK cells, and B cells are not present within the mononuclear cells.

FIG. 2 is a graph plotted by measuring the number of the peripheral blood mononuclear cells (PBMCs) in a group in which PBMCs separated from a human are treated with only IL-2 (◇, PBMC), a group in which PBMCs are co-cultured with an irradiated Jurkat cell line in the presence of IL-2 (■, PBMC+Jurkat), a group in which PBMCs are co-cultured with an irradiated EBV-LCL cell line in the presence of IL-2 (▲, PBMC+LCL), and a group in which PBMCs are co-cultured with the irradiated Jurkat cell line and the irradiated EBV-LCL cell line in the presence of IL-2 (×, PBMC+Jurkat+LCL).

FIG. 3 is a graph plotted by measuring the number of the NK cells in the group in which PBMCs are treated with only IL-2 (◇, PBMC), the group in which PBMCs are co-cultured with an irradiated Jurkat cell line in the presence of IL-2 (■, PBMC+Jurkat), the group in which PBMCs are co-cultured with an irradiated EBV-LCL cell line in the presence of IL-2 (▲, PBMC+LCL), and the group in which PBMCs are co-cultured with the irradiated Jurkat cell line and the irradiated EBV-LCL cell line in the presence of IL-2 (×, PBMC+Jurkat+LCL).

FIG. 4A shows the results obtained by analyzing enrichment levels of the NK cells using a flow cytometer in the group in which PBMCs are treated with only IL-2 (PBMC), the group in which PBMCs are co-cultured with an irradiated Jurkat cell line in the presence of IL-2 (PBMC+Jurkat), the group in which PBMCs are co-cultured with an irradiated EBV-LCL cell line in the presence of IL-2 (PBMC+LCL), and the group in which PBMCs are co-cultured with the irradiated Jurkat cell line and the irradiated EBV-LCL cell line in the presence of IL-2 (PBMC+Jurkat+LCL).

FIG. 4B is a graph illustrating the enrichment levels of the NK cells in the group in which PBMCs are treated with only IL-2 (◇, PBMC), the group in which PBMCs are co-cultured with an irradiated Jurkat cell line in the presence of IL-2 (■, PBMC+Jurkat), the group in which PBMCs are co-cultured with an irradiated EBV-LCL cell line in the presence of IL-2 (▲, PBMC+LCL), and the group in which PBMCs are co-cultured with the irradiated Jurkat cell line and the irradiated EBV-LCL cell line in the presence of IL-2 (×, PBMC+Jurkat+LCL).

FIG. 5 is a graph plotted by evaluating the abilities of the NK cells to kill cancer cells in a group in which PBMCs are co-cultured with an irradiated Jurkat cell line in the presence of IL-2 (♦), a group in which PBMCs are co-cultured with an irradiated EBV-LCL cell line in the presence of IL-2 (×), and a group (*) in which PBMCs are co-cultured with both the irradiated Jurkat cell line and the EBV-LCL cell line, in the presence of IL-2.

FIG. 6 shows the results obtained by analyzing activation of the NK cells prepared according to one exemplary embodiment of the present invention.

BEST MODE

These and other advantages and features of the present invention and method of achieving them will be apparent from the following description of preferred embodiments, with reference to the accompanying drawings. However, the present invention is not limited to the following embodiments but will be embodied in various forms. That is, the embodiments of the present invention play a role of making the disclosure of the present invention complete, and are provided to inform a person who has an ordinary knowledge and skill in the art to which this invention belongs. This invention should be defined based on the scope of claims.

EXAMPLES

Example 1: Preparation of NK Cells from Peripheral Blood Mononuclear Cells

Human blood was collected and centrifuged at 2,500 rpm for 30 minutes in Ficoll (Ficoll-paque™ PLUS, GE Health-Care), and peripheral blood mononuclear cells (PBMCs) were separated from a buffy coat. Thereafter, the PBMCs were stained with Tryphan Blue. Then, damaged cells were removed, and only unstained cells were counted using a hematocytometer.

A Jurkat cell line and an EBV-LCL cell line used as feeder cells were cultured at 37° C. in human RPMI media, which were obtained by adding 10% FBS and 1% penicillin/streptomycin to an RPMI1640 medium under a 5% $CO_2$ condition. A hRPMI medium supplemented with 500 U/ml of IL-2 was added once every 2 to 3 days, the cells were harvested at an interval of 5 days, and a fresh hRPMI medium supplemented with IL-2 was added.

Cell counts were measured using a hematocytometer, and the Jurkat cell line and the EBV-LCL cell line, both of which were present at a concentration of $1\times10^6$/ml, were irradiated with radiation of 100 Gy at an intensity of 2.22 Gy/min.

A hRPMI medium supplemented with 500 U/ml of IL-2 was put into wells of a 24-well plate, and the irradiated Jurkat cell line, the irradiated EBV-LCL cell line, and the previously separated mononuclear cells were cultured at a ratio of 1:0.5:0.5 and a temperature of 37° C. in an incubator into which 5% $CO_2$ was being supplied (an experimental group).

Also, a group in which the mononuclear cells were cultured in the presence of IL-2 in the same manner as described above without adding a feeder cell line (control 1), a group in which the mononuclear cells were cultured with irradiated Jurkat cells in the presence of IL-2 (control 2), and a group in which the mononuclear cells were cultured with irradiated EBV-LCL cells in the presence of IL-2 (control 3) were used as the controls.

Example 2: Measurement of Ability to Proliferate NK Cells

To determine an effect of the feeder cells on proliferation of the NK cells, the NK cells in the experimental group defined in Example 1, control 1, control 2, and control 3 were counted on 0 day, $5^{th}$ day, $11^{th}$ day, and $14^{th}$ day, and stained using antibodies against fluorescence-labeled CD56 and CD3. Thereafter, the NK cells were analyzed using flow cytometry to assay the groups of NK cells (CD56+, CD3−). Subsequently, the NK cells were counted using the sum of the enrichment levels of the PBMCs and NK cells.

As a result, it was revealed that the PBMCs increased approximately 147 times higher in the case of the experimental group (×, PBMC+Jurkat+LCL) in which both the Jurkat cells and the EBV-LCL cells were co-cultured with PBMCs than in the case of control 1 (◇, PBMC), control 2 (■, PBMC+Jurkat), or control 3 (▲, PBMC+LCL) on the $14^{th}$ day of culturing, as shown in FIG. 2. Also, it was revealed that the NK cells increased approximately 800 times higher in the experimental group than the controls on the $14^{th}$ day of culturing when both the Jurkat cells and the EBV-LCL cells were co-cultured with PBMCs.

Example 3: Measurement of Enrichment Level of NK Cells

To analyze an effect of the feeder cells and the cytokines on enrichment of the NK cells, the NK cells were stained using fluorescence-labeled CD56 and CD3 antibodies on 0 day, $5^{th}$ day, $11^{th}$ day, and $14^{th}$ day of culturing, and analyzed for the experimental group of Example 1, control 1, control 2, and control 3 using flow cytometry. As a result, it was revealed that the percentage of the NK cell phenotypes, CD56+ and CD3 cells, increased to 70% or more when the mononuclear cells were co-cultured with the Jurkat cells and the EBV-LCL cells after the 14-day culture (FIG. 4A). FIG. 4B is a graph illustrating the enrichment levels of the NK cells, as measured on the $14^{th}$ day of culturing using flow cytometry.

Example 4: Measurement of Ability of NK Cells Prepared According to One Exemplary Embodiment of the Present Invention to Kill Cancer Cells To evaluate an ability of the NK cells, which were prepared using the irradiated Jurkat cell line and irradiated EBV-LCL cell line of Example 1 as the feeder cells, to kill cancer cells, a $^{51}$Cr release assay was performed using tumor cells (K562, Jurkat) as target cells.

First, the cancer cells K562 and the Jurkat cells were counted, and labeled with an isotope, $^{51}$Cr, and then reacted for an hour in a cell incubator. The isotope-labeled cancer cells were washed three times with a hRPMI medium to remove the isotope. The cells obtained in the experimental group of Example 1, control 2, and control 3 were counted using a hematocytometer, and then co-cultured with the isotope-labeled cancer cells at a ratio of 10:1, 3:1, or 1:1 for 4 hours. After 4 hours, the cells were centrifuged at 2,500 rpm for 5 minutes, and the supernatant was put into a tube and measured using a gamma counter.

As shown in FIG. 5, it could be seen that the ability of the NK cells to kill cancer cells was observed to be similar to that of control 2 (♦) in which the IL-2 and irradiated Jurkat cell line were used, in the case of the control 3 (×) in which the IL-2 and irradiated EBV-LCL cell line were used, and experimental group (*) in which both the irradiated Jurkat cell line and EBV-LCL cell line were co-cultured. Also, it was confirmed that the NK cells had a significant ability to kill cancer cells even when the effector cells and the target cells were present at an E:T ratio of 1:1.

As seen from these results, it could be seen that the peripheral blood mononuclear cells according to one exemplary embodiment of the present invention which were treated with the IL-2, the irradiated Jurkat cells, and the irradiated EBV-LCL cell, were enriched to become the NK cells and also had a superior ability to kill cancer cells.

Example 5: Measurement of Activation of NK Cells Prepared According to One Exemplary Embodiment of the Present Invention Example 4 showed that the NK cells, which were prepared using the irradiated Jurkat cell line and the irradiated EBV-LCL cell line prepared in Example 1 as the feeder cells, had a high ability to kill cancer cells. Thus, evaluating the presence of activation markers, expression of various NK cell-related activation and inhibitory receptors in the NK cells, which were cultured for 11 days, was examined using flow cytometry.

As shown in FIG. 6, it could be seen that the cell adhesion molecules such as ICAM-1, CD11a, CD48, CD2, CD49d, and CD58, the activation receptors such as NKp30, NKp44, 2B4, DNAM-1, and NKG2D, and the activation markers such as CD69, and CD25 were expressed at an increased level; the chemokine receptors such as CD183, CD184, and CCR7 were expressed at a slightly increased level; and the inhibitory receptors such as CD158a, CD158b, CD94, NKB1, and KIRNKAT2 were expressed at an increased level.

What is claimed is:

1. A method for treating a cancer in a subject in need thereof, wherein the method comprises:
   expanding natural killer cells in a co-culture comprising peripheral blood mononuclear cells and feeder cells, wherein the feeder cells comprise irradiated Jurkat cells and irradiated Epstein-Barr virus transformed lymphocyte continuous cell line (EBV-LCL) cells and the co-culture is in the presence of one or more cytokines; and
   administering an effective amount of a composition comprising the expanded natural killer cells to the subject, thereby treating the cancer.

2. The method of claim 1, wherein the one or more cytokines is selected from IL-2, IL-15, IL-21, Flt3-L, SCF, or IL-7.

3. The method of claim 2, wherein the one or more cytokines is IL-2.

4. The method of claim 3, wherein the IL-2 is present at a concentration of 500 U/ml.

5. The method of claim 1, wherein the peripheral blood mononuclear cells are obtained from a normal person or a person suffering from the cancer.

6. The method of claim 1, wherein the peripheral blood mononuclear cells are obtained from the subject.

7. The method of claim 1, wherein the peripheral blood mononuclear cells are obtained from a healthy subject.

8. The method of claim 1, wherein each of the irradiated Jurkat cells or the irradiated EBV-LCL cells is obtained by treatment with radiation of 100 to 500 Gy.

9. The method of claim 1, wherein the peripheral blood mononuclear cells are co-cultured for 5 days to 14 days.

10. The method of claim 1, wherein the peripheral blood mononuclear cells and feeder cells are mixed at a ratio of 1:0.5:0.5 during the co-culturing.

11. The method of claim 1, wherein the co-culturing comprises adding the irradiated Jurkat cells, the irradiated EBV-LCL cells and the one or more cytokines on the 1st to 15th day.

12. The method of claim 1, wherein the cancer comprises lung cancer, liver cancer, breast cancer, or blood cancer.

13. A method for treating a cancer in a subject in need thereof, the method comprising:

providing a composition comprising natural killer cells, wherein providing the composition comprises expanding natural killer cells in a co-culture comprising peripheral blood mononuclear cells and feeder cells for 5 days to 14 days, wherein the feeder cells comprise irradiated Jurkat cells and irradiated Epstein-Barr virus transformed lymphocyte continuous cell line (EBV-LCL) cells, wherein the co-culture is in the presence of one or more cytokines, wherein the one or more cytokines comprise IL-2, and wherein the peripheral blood mononuclear cells and feeder cells are mixed at a ratio of 1:0.5:0.5 during the co-culturing; and administering an effective amount of the composition to the subject, thereby treating the cancer.

14. The method of claim 13, wherein the one or more cytokines are IL-2.

15. The method of claim 13, wherein the cancer comprises lung cancer, liver cancer, breast cancer, or blood cancer.

\* \* \* \* \*